US008864999B2

(12) United States Patent
Brandvold et al.

(10) Patent No.: US 8,864,999 B2
(45) Date of Patent: *Oct. 21, 2014

(54) METHODS FOR REGENERATING ACIDIC ION-EXCHANGE RESINS AND REUSING REGENERANTS IN SUCH METHODS

(75) Inventors: Timothy A. Brandvold, Arlington Heights, IL (US); Stanley J. Frey, Palatine, IL (US); Vasken Abrahamian, Morton Grove, IL (US); Thomas Traynor, Buffalo Grove, IL (US)

(73) Assignee: UOP LLC, Des Plaines, IL (US)

( * ) Notice: Subject to any disclaimer, the term of this patent is extended or adjusted under 35 U.S.C. 154(b) by 1035 days.

This patent is subject to a terminal disclaimer.

(21) Appl. No.: 12/646,327

(22) Filed: Dec. 23, 2009

(65) Prior Publication Data

US 2011/0146145 A1    Jun. 23, 2011

(51) Int. Cl.
*B01D 15/36* (2006.01)
*G01N 30/50* (2006.01)
*B01J 49/00* (2006.01)
*B01D 15/20* (2006.01)
*C10L 1/02* (2006.01)
*B01D 41/02* (2006.01)
*G01N 30/96* (2006.01)

(52) U.S. Cl.
CPC .......... *B01J 49/0069* (2013.01); *B01D 15/362* (2013.01); *B01J 49/0008* (2013.01); *G01N 30/96* (2013.01); *B01D 15/20* (2013.01); *B01D 15/203* (2013.01); *G01N 30/50* (2013.01); *C10L 1/02* (2013.01); *C10G 2300/1011* (2013.01)
USPC ........................... 210/670; 210/660; 210/792

(58) Field of Classification Search
CPC ...... B01D 15/08; B01D 15/20; B01D 15/203; B01D 15/36; B01D 15/361; B01D 15/362; G01N 30/50; G01N 30/96; B01J 49/0008; B01J 49/0069
USPC ................................. 210/671, 677, 792, 791
See application file for complete search history.

(56) References Cited

U.S. PATENT DOCUMENTS 2,566,353 A * 9/1951 Mills .............................. 208/91
3,309,356 A    3/1967 Esterer (Continued)

FOREIGN PATENT DOCUMENTS

BR    8304158    7/1984
CN    101294085    10/2008

(Continued)

OTHER PUBLICATIONS

Sukhbaatar, B., Separation of Organic Acids and Lignin Fraction From Bio-Oil and Use of Lignin Fraction in Phenol-Formaldehyde Wood Adhesive Resin, Masters Thesis, Mississippi State, Aug. 2008.

(Continued)

*Primary Examiner* — Katherine Zalasky
(74) *Attorney, Agent, or Firm* — Mark R Willis

(57) ABSTRACT

Methods for regenerating acidic ion-exchange resins and reusing regenerants in such methods are provided. A spent ion-exchange resin is contacted with an alcohol ion-exchange regenerant. The spent ion-exchange resin is thereafter contacted with an acidic ion-exchange regenerant to recharge the acidic ion-exchange resin to produce a regenerated acidic ion-exchange resin. Metal- and water-containing biomass-derived pyrolysis oil is then contacted with the regenerated acidic ion-exchange resin to produce low metal, water-containing biomass-derived pyrolysis oil. The regenerated acidic ion-exchange resin may be recycled. The spent alcohol and acid ion-exchange regenerants may be recovered and recycled.

19 Claims, 4 Drawing Sheets

(56) References Cited

U.S. PATENT DOCUMENTS

| | | | |
|---|---|---|---|
| 3,313,726 A * | 4/1967 | Campbell et al. | ............... 521/26 |
| 4,064,043 A | 12/1977 | Kollman | |
| 4,204,915 A | 5/1980 | Kurata et al. | |
| 4,548,615 A | 10/1985 | Longchamp et al. | |
| 4,897,178 A | 1/1990 | Best et al. | |
| 5,371,212 A | 12/1994 | Moens | |
| 6,193,837 B1 | 2/2001 | Agblevor et al. | |
| 6,844,420 B1 | 1/2005 | Freel et al. | |
| 6,875,341 B1 | 4/2005 | Bunger et al. | |
| 7,319,168 B2 | 1/2008 | Sanada | |
| 2007/0141222 A1 | 6/2007 | Binder et al. | |
| 2008/0161615 A1 | 7/2008 | Chapus et al. | |
| 2008/0312476 A1 | 12/2008 | McCall | |
| 2008/0318763 A1 | 12/2008 | Anderson | |
| 2009/0077868 A1 | 3/2009 | Brady et al. | |
| 2009/0078611 A1 | 3/2009 | Marker et al. | |
| 2009/0082603 A1 | 3/2009 | Kalnes et al. | |
| 2009/0188158 A1 | 7/2009 | Morgan | |
| 2009/0193709 A1 | 8/2009 | Marker et al. | |
| 2009/0253947 A1 * | 10/2009 | Brandvold et al. | ............... 585/14 |
| 2011/0146135 A1 | 6/2011 | Brandvold | |
| 2011/0146140 A1 | 6/2011 | Brandvold et al. | |
| 2011/0146141 A1 | 6/2011 | Frey et al. | |
| 2012/0317871 A1 | 12/2012 | Frey et al. | |

FOREIGN PATENT DOCUMENTS

| | | |
|---|---|---|
| CN | 101381611 | 3/2009 |
| CN | 101544901 | 9/2009 |
| CN | 101550347 | 10/2009 |
| EP | 0718392 B1 | 9/1999 |
| SE | 9903742-6 | 7/2004 |
| WO | 2007045093 A1 | 4/2007 |
| WO | 2007050030 A1 | 5/2007 |
| WO | 2008020167 A2 | 2/2008 |
| WO | 2008092557 A2 | 8/2008 |

OTHER PUBLICATIONS

Goesele, W., and Alt, C., Filtration, Wiley-VCH Verlag GmbH & Co. KGaA, Weinheim, 10.1002/14356007.b02 10, 2005.

Filtration, Kirk-Othmer Encyclopedia of Chemical Technology 5th Edition. vol. 11., John Wiley & Sons, Inc., Feb. 2005.

Bridgwater, A.V., Principles and practice of biomass fast pyrolysis processes for liquids, Journal of Analytical and Applied Pyrolysis, 51 (1999) pp. 3-21.

Mohan, D., et al., Pyrolysis of Wood/Biomass for Bio-oil: A Critical Review., Energy & Fuels 2006, No. 20, pp. 848-849.

Scott, D., et al, Pretreatment of poplar wood for fast pyrolysis: rate of cation removal, Journal of Analytical and Applied Pyrolysis, 57 (2000) pp. 169-176.

Hoekstra, E.,et al., Fast Pyrolysis of Biomass in a Fluidized Bed Reactor : In Situ Filtering of the Vapors. Ind. Eng. Chem. Res., 2009, 48 (10), 4744-4756, Apr. 21, 2009.

Scahill, J., et al., Removal of Residual Char Fines from Pyrolysis Vapors by Hot Gas Filtration. C. Center for Renewable Chemical Technologies and Materials, National Renewable Energy Laboratory (1997), 253-266.

Jumming et al., "Bio-oil upgrading by means of ethyl ester production in reactive distillation to remove water and to improve storage and fuel characteristics", Biomass and Bioenergy, 2008, pp. 1056-1061, vol. 32.

* cited by examiner

METHODS FOR REGENERATING ACIDIC ION-EXCHANGE RESINS AND REUSING REGENERANTS IN SUCH METHODS

CROSS-REFERENCE TO RELATED APPLICATIONS

This application is related to co-pending U.S. application Ser. No. 12/646,203 entitled "LOW WATER BIOMASS-DERIVED PYROLYSIS OIL AND PROCESSES FOR PRODUCING THE SAME", U.S. application Ser. No. 12/646,239 entitled "LOW METAL BIOMASS-DERIVED PYROLYSIS OILS AND PROCESSES FOR PRODUCING THE SAME", and U.S. application Ser. No. 12/646,288 entitled "LOW METAL, LOW WATER BIOMASS-DERIVED PYROLYSIS OILS AND METHODS FOR PRODUCING THE SAME", filed concurrently herewith on Dec. 23, 2009, and which are incorporated by reference herein in their entirety.

FIELD OF THE INVENTION

The present invention generally relates to biofuels and methods for producing biofuels, and more particularly relates to methods for regenerating acidic ion-exchange resins and reusing ion-exchange regenerants in such methods.

DESCRIPTION OF RELATED ART

Fast pyrolysis is a process during which organic biomass materials, such as wood waste, agricultural waste, etc. are rapidly heated to about 450° C. to about 600° C. in the absence of air using a process reactor. Under these conditions, organic vapors, pyrolysis gases and ash (char) are produced. The vapors are condensed to biomass-derived pyrolysis oil. Biomass-derived pyrolysis oil can be burned directly as fuel for certain boiler and furnace applications, and can also serve as a potential feedstock in catalytic processes for the production of fuels in petroleum refineries. Biomass-derived pyrolysis oil has the potential to replace up to 60% of transportation fuels, thereby reducing the dependency on conventional petroleum and reducing its environmental impact.

However, biomass-derived pyrolysis oil is a complex, highly oxygenated organic liquid having properties that currently limit its utilization as a biofuel. For example, metals in the conventional biomass-derived pyrolysis oil limit its commercial applications. Metals dissolved in the biomass-derived pyrolysis oil contribute to ash content of the oil upon combustion. It is desirable to reduce and minimize the ash content in the biomass-derived pyrolysis oil because such ash raises the total ash and particulate emissions when the biomass-derived pyrolysis oil is burned for consumption as a fuel. Environmental restrictions may limit such total emissions. In addition, when the biomass-derived pyrolysis oil is used as feedstock in catalytic processes to make transportation fuel, the metals in the oil foul downstream equipment and inhibit or inactivate catalysts. The removal of metal cations from biomass-derived pyrolysis oil to produce low metal biomass-derived pyrolysis oil is therefore desirable for utilization of biomass-derived pyrolysis oil as a biofuel.

While ion-exchange resins are used to remove metals from aqueous solutions, they have not been effective in removing metals from biomass-derived pyrolysis oil because of their susceptibility to fouling. Ion-exchange resin is known to foul irreversibly when exposed to non-polar oils such as those found in the water insoluble tars of biomass-derived pyrolysis oil. The oil will readily coat each ion-exchange bead and severely inhibit the bead's ability to adsorb ionic materials from the organic stream. As the oil is also sticky, it will result in agglomeration of the ion-exchange beads, producing channeling of the bed. The agglomeration can also significantly affect backwashing. The remedy for fouling by non-polar oils is a detergent wash. However, such washes are not entirely effective.

In addition, while spent ion-exchange resins, if not too badly fouled, can be regenerated, conventional regeneration requires an extremely labor intensive and costly method. In addition, the use of conventional acidic ion-exchange regenerants, such as a concentrated hydrochloric or sulfuric acid solution, may be costly and disposal of the spent acidic ion-exchange regenerants may be difficult.

Other properties that limit the commercial application of conventional biomass-derived pyrolysis oil include its high water content. Conventional biomass-derived pyrolysis oil typically contains about 20-33% by weight water with high acidity (TAN>150). Biomass-derived pyrolysis oil may often be stored in tanks or the like for long periods of time resulting in increases in viscosity, phase separation and/or solids formation during such storage. The high water content of biomass-derived pyrolysis oil increases the storage instability of the oil. Biomass-derived pyrolysis oil cannot be conventionally distilled to completely remove water, as phase separation and/or solids formation result as volatiles are removed. If conventional biomass-pyrolysis oil is heated to elevated temperatures (e.g., about 150° C.) some volatiles may vaporize initially, but the majority of the oil solidifies and/or chars. At lower temperatures, phase separation occurs, albeit more slowly.

Conventional biomass-derived pyrolysis oil may also be contaminated with char fragments and other insolubles produced during biomass pyrolysis. Char contributes to thermal instability of the oil. The char content is correlated with increases in viscosity, phase separation and/or solids formation during storage. Separation of the char fragments from the biomass-derived pyrolysis oil has proven very difficult. For example, conventional liquid filtration is difficult as the liquid biomass-derived pyrolysis oil can have a gel-like consistency.

Accordingly, it is desirable to provide low metal, low water biomass-derived pyrolysis oils and methods for producing the same. In addition, it is also desirable to remove insolubles including the reduction of char content from the liquid biomass-derived pyrolysis oil product. It is also desirable to provide methods for regenerating acidic ion-exchange resins and reusing ion-exchange regenerants in such methods. Furthermore, other desirable features and characteristics of the present invention will become apparent from the subsequent detailed description of the invention and the appended claims, taken in conjunction with the accompanying drawings and this background of the invention.

SUMMARY OF THE INVENTION

Methods are provided for the regeneration of a spent acidic ion-exchange resin and recycling thereof. In accordance with an exemplary embodiment of the present invention, the method comprises contacting a spent ion-exchange resin with an alcohol ion-exchange regenerant. The spent ion-exchange resin is thereafter contacted with an acidic ion-exchange regenerant to recharge the spent ion-exchange resin to produce a regenerated acidic ion-exchange resin. Metal- and water-containing biomass-derived pyrolysis oil is then contacted with the regenerated acidic ion-exchange resin to produce low metal, low water biomass-derived pyrolysis oil which contains residual alcohol ion-exchange regenerant to improve its phase stability.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Various exemplary embodiments of the present invention are directed to low metal, low water biomass-derived pyrolysis oils and methods for producing the same and methods for regenerating acidic ion-exchange resins and reusing ion-exchange regenerants for use in the methods for producing low metal, low water biomass-derived pyrolysis oil. It should be appreciated that while the oil produced according to exemplary embodiments of the present invention is generally described herein as a "low metal, low water biomass-derived pyrolysis oil", this term generally includes any oil produced having a lower total metal concentration and weight percent (wt %) of water than the starting metal- and water-containing biomass-derived pyrolysis oil as a result of ion exchange and distillation, according to exemplary embodiments of the present invention. The starting metal- and water-containing biomass-derived pyrolysis oil is a conventional biomass-derived pyrolysis oil and may be referred to herein simply as "biomass-derived pyrolysis oil."

Figure 1:
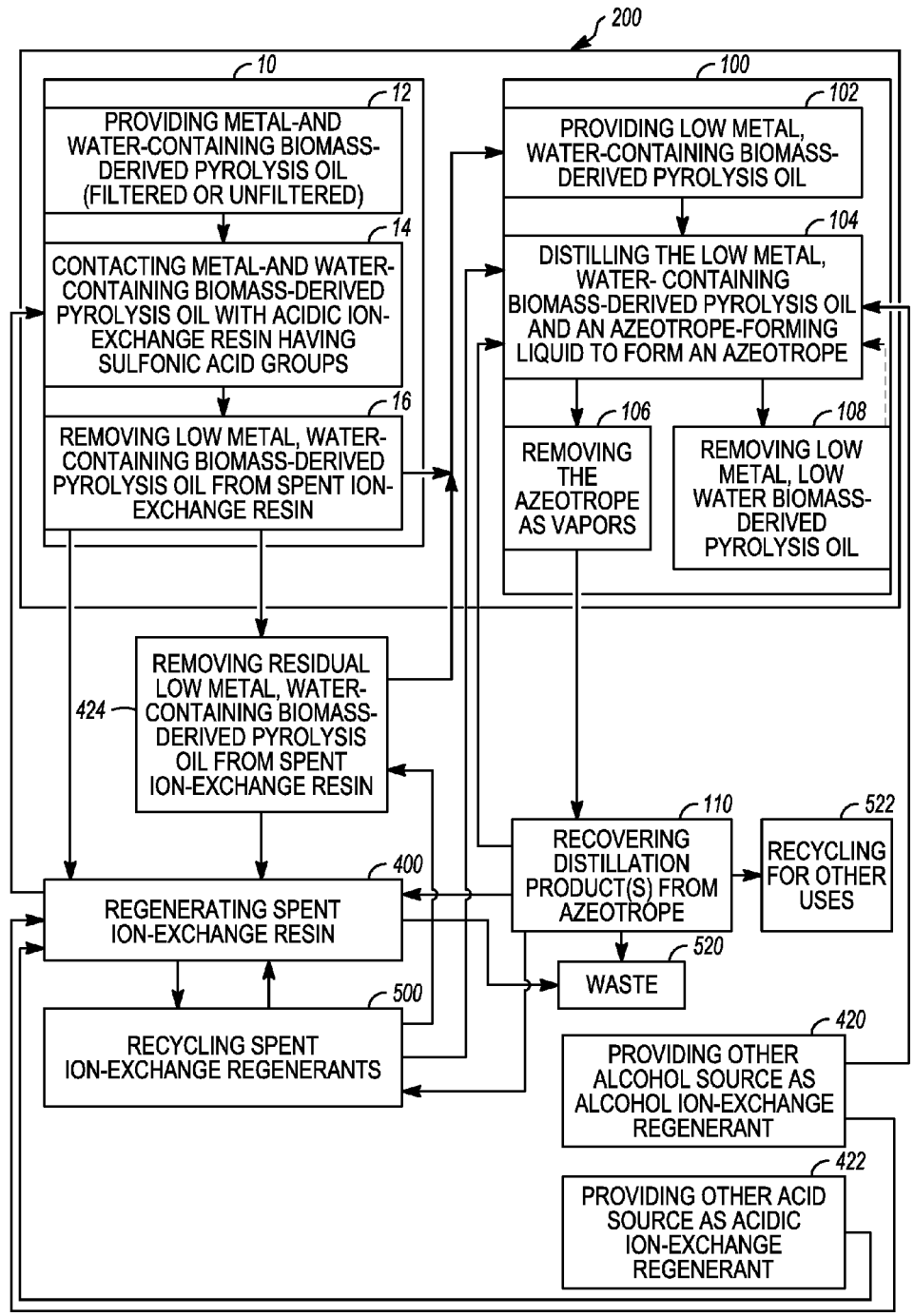
FIG. 1 is a flow diagram of a method for producing low metal, low water biomass-derived pyrolysis oil and regenerating and reusing an ion-exchange resin and regenerants in such method, according to exemplary embodiments of the present invention.

As shown in FIG. 1, a method 200 for producing low metal, low water biomass-derived pyrolysis oil comprises a process 10 for the production of low metal, water-containing biomass-derived pyrolysis oil and a process 100 for the production of low water biomass-derived pyrolysis oil. The process 10 for the production of low metal, water-containing biomass-derived pyrolysis oil is described in concurrently filed application Ser. No. 12/646,239, filed Dec. 23, 2009 by certain of the same named inventors, and incorporated by reference herein in its entirety. The process 100 for the preparation of low water biomass-derived pyrolysis oil is described in concurrently filed application Ser. No. 12/646,203, filed Dec. 23, 2009 by certain of the same named inventors, and incorporated by reference herein in its entirety. As used herein, "low metal, water-containing biomass-derived pyrolysis oil" generally includes any treated oil having a lower total metal concentration than the starting metal- and water-containing biomass-derived pyrolysis oil as a result of ion-exchange. "Low water biomass-derived pyrolysis oil" as used herein generally includes any treated oil having a lower weight percent (wt %) of water than in the starting metal- and water-containing biomass-derived pyrolysis oil as a result of distillation.

Method 200 begins by providing metal- and water-containing biomass-derived pyrolysis oil from a source such as a feed tank or other source operative to provide such metal- and water-containing biomass-derived pyrolysis oil (step 12). Biomass-derived pyrolysis oil composition is somewhat dependent on feedstock and processing variables. The total metal concentration in the biomass-derived pyrolysis oil generally ranges from about 0.02 weight percent (wt %) to about 0.5 weight percent (wt %) and typically contains alkali metals, alkaline earth metals, transition metals, and heavy metals. Metals are indigenous to all biomass and thus to the starting biomass-derived pyrolysis oil. Unless volatile under combustion conditions, these metals contribute to the ash content of the oil upon combustion. The biomass-derived pyrolysis oil typically contains about 20-33% by weight water with high acidity (TAN>150). Biomass-derived pyrolysis oil is available from, for example, Ensyn Technologies Inc., of Ontario, Canada.

The biomass-derived pyrolysis oil may be produced, for example, from fast pyrolysis of wood biomass in a pyrolysis reactor. However, the invention is not so limited. Virtually any form of biomass can be considered for pyrolysis to produce biomass-derived pyrolysis oil. In addition to wood, biomass-derived pyrolysis oil may be derived from biomass material such as bark, agricultural wastes/residues, nuts and seeds, algae, grasses, forestry residues, cellulose and lignin, or the like. The biomass-derived pyrolysis oil may be obtained by different modes of pyrolysis, such as fast pyrolysis, vacuum pyrolysis, catalytic pyrolysis, and slow pyrolysis (also known as carbonization) or the like.

The biomass-derived pyrolysis oil may be filtered to substantially prevent plugging of the ion-exchange resin with the char and other insolubles that collect in the biomass-derived pyrolysis oil during the pyrolysis process. In addition, filtering the starting biomass-derived pyrolysis oil increases the thermal stability of the low metal, low water biomass-derived pyrolysis oil produced in accordance with exemplary embodiments of the present invention as well as the intermediate oils produced by processes 10 and 100. As used herein, "thermal stability" means the ability of the oil to resist changes in chemical composition and maintain phase stability as its temperature changes or with extended storage time. Filtration helps to lower viscosity, maintain homogeneity by improving phase stability, improve clarity, and increase pumpability of the oils produced in accordance with exemplary embodiments of the present invention. The starting biomass-derived pyrolysis oil may be contacted with one or more filters (and filter media) for a selected period of time to produce a filtrate comprised of filtered biomass-derived pyrolysis oil and a filter cake. The one or more filters may be used sequentially for treating the same volume of oil. The one or more filters may be of the same or different type using one or more of vacuum, gravity, or pressure filtration. The filtrate is removed from the filter cake and the filtrate (the biomass-derived pyrolysis oil having increased thermal stability) is recovered. For pressure filtration, pressurized gas such as nitrogen, air, or the like may be supplied on the input side of the filter to accelerate filtration. Pressures (atm., absolute) from about 1 atmosphere absolute pressure to about 8 atmospheres absolute may be used. The period of time required for filtration is dependent on volume and viscosity of the oil being filtered, the amount and particle size of solids to be removed, the filter media (composition and pore size), and filtration pressure and temperature. For vacuum filtration, negative pressure (i.e., a vacuum) of about 0.10 atm absolute to about 0.95 atm absolute may be supplied on the output side of the filter. No pressure is used for gravity filtration.

The filter may be comprised of a filter medium selected from the group consisting of nitrocellulose, cellulose acetate, glass fiber, polymeric (such as polytetrafluoroethylene and nylon-6), wire mesh, sintered metal, and the like, and can be provided in a variety of shapes and sizes. The filter medium preferably has a pore diameter smaller than the char and other insolubles in the biomass-derived pyrolysis oil. Filter pore diameters vary widely depending on the materials used, but typical pore diameters range from about 0.1 to about 100 micrometers. Preferred pore diameters range from about 5 to about 50 micrometers. Exemplary filter/filter medium and filtration equipment suppliers include Whatman Plc (Kent, U.K.), Millipore Corporation (Billerica, Mass.), Filtrex Corporation (Attleboro, Mass.), Mott Corporation (Farmington, Conn.) and Pall Corporation (Port Washington, N.Y.).

The biomass-derived pyrolysis oil, the filter, or both may be heated to a temperature of about 30° C. to about 55° C., preferably about 45° C. to increase the filtration rate. Heat is supplied to the filter by any conventional means. As is known in the filtration art, a filter aid may be used to improve filtration of the biomass-derived pyrolysis oil. Suitable exemplary filter aids include Celite®, Norit®, and diatomaceous earth filter aids.

Filter performance is often defined by "flux" which is the volume of feed (biomass-derived pyrolysis oil) filtered per unit filter area per unit time. As an example only, if 0.672 liters of biomass-derived pyrolysis oil were filtered through a circular filter with a diameter of 11 cm (area=$\pi r^2$=3.1416*(5.5 cm)$^2$=95 cm$^2$) and a constant mass of filtrate was obtained in about one hour, the filter flux in this example is approximately 0.672 L/(3.14*95 cm$^2$)/1 hr=0.007 L/hr/cm$^2$. In general, higher filter flux is preferred, but liquid filter fluxes in the range of about 0.001 L/hr/cm$^2$ to about 10 L/hr/cm$^2$ are considered acceptable.

Method 200 continues with contacting the biomass-derived pyrolysis oil, whether filtered or unfiltered, with an ion-exchange resin (step 14). The biomass-derived pyrolysis oil that contacts the ion-exchange resin undergoes ion exchange such that metal ions are captured by the ion-exchange resin. More specifically, the ion-exchange resin contains sulfonic acid at its active sites. When the biomass-derived pyrolysis oil contacts the resin, the metals preferentially migrate out of the oil to the active sites on the ion-exchange resin. The metals in the biomass-derived pyrolysis oil are replaced by hydrogen ions.

The ion-exchange can be accomplished by either a batch method or a continuous column method. In the batch method, the ion-exchange resin and starting biomass-derived pyrolysis oil are contacted by mixing the resin and starting oil in a resin vessel, batch tank, or the like. A given weight of ion-exchange resin is added to a known volume of starting biomass-derived pyrolysis oil, as hereinafter described. The amount of ion-exchange resin added to the fixed amount of oil is typically an excess of resin (based on theoretical resin capacity, as defined below). The optimum resin to oil ratio is determined experimentally and is impacted by temperature and exposure time. The resin/oil mixture is agitated for about 0.5 hours to about 24 hours, preferably about 0.5 to about 4 hrs (hereinafter "the exposure time") at a temperature of about 10° C. to about 120° C., preferably from about 20° C. to about 60° C. Samples of the treated oil may be collected and analyzed for metal content, as hereinafter described.

In the continuous column method, the ion-exchange resin and the biomass-derived pyrolysis oil are contacted by passing the biomass-derived pyrolysis oil through a column (of one or more "beds") containing the ion-exchange resin. The resin temperature may be from about 10° C. to about 120° C., preferably from about 20° C. to about 60° C. The biomass-derived pyrolysis oil is passed through the column by positive pressure flow or by gravity flow. When pressure is applied, the absolute pressure is from greater than 0 KPa to about 13790 KPa (0 to about 2000 psi), preferably from greater than 0 KPa to about 689.5 KPa (greater than 0 psi to about 100 psi), and most preferably from about 13.8 KPa to about 206.8 KPa (about 2 psi to about 30 psi). When no pressure is applied, the low-metal biomass-derived pyrolysis oil passes downward through the column and is allowed to slowly elute gravimetrically.

The biomass-derived pyrolysis oil is passed over the ion-exchange resin at a Liquid Hourly Space Velocity (LHSV) of about 0.1-20 hr$^{-1}$, preferably about 1-10 hr$^{-1}$. The faster the Liquid Hourly Space Velocity (LHSV), the less time there is for the ion-exchange. When the Liquid Hourly Space Velocity (LHSV) is reduced, the concentration of the selected metal ions in the treated oil is reduced significantly.

When metal levels in the treated biomass-derived pyrolysis oil reach a target concentration, or when metal concentration is constant (as determined by repeat measurements) over an extended time period, contact between the oil and the resin may be concluded and ion-exchange is deemed "complete". Metal concentrations in the oil may be measured by Atomic Absorption Spectroscopy (AAS), Inductively-Coupled Plasma-Atomic Absorption Spectroscopy (ICP-AAS) or other known methods.

The volume capacity of the ion-exchange resin ($VC_r$) for both batch and continuous column methods is the volume of resin needed to completely ion-exchange a given mass of oil and is determined by the equation:

$$VC_r(\text{mL resin/kg oil}) = (\Sigma_i (C_i * 1000 \text{ g/kg})/MW_i) * V_i * 1000 \text{ meq/eq}/(TC_r * D_r)$$

wherein:
$C_i$ is the concentration of metal i in the biomass-derived pyrolysis oil in gram metal/gram oil;
$MW_i$ is the molecular weight of metal in g/mol;
$V_i$ is the valency (charge) of metal i in solution;
$D_r$ is the ion-exchange resin density in g/mL; and
$TC_r$ is the theoretical capacity of resin r. Theoretical capacity ($TC_r$) is often expressed in terms of milliequivalents ions/gram resin.

The maximum volume of oil (in liters) that can be processed per unit volume of ion-exchange resin in both batch and continuous column methods is expressed as:

$$V_{oil} = V_r/(VC_r * D_{feed}))$$

wherein:
$V_{oil}$ is the volume of biomass-derived pyrolysis oil in liters;
$D_{feed}$ is the feed oil (the starting biomass-derived pyrolysis oil) density (in kilograms/liter);
$V_r$ is the resin volume in milliliters; and
$VC_r$ is the volume capacity of acidic ion-exchange resin to a given mass of metal-containing biomass-derived pyrolysis oil as determined above and expressed in mL resin/kg of biomass-derived pyrolysis oil. The $V_{oil}/V_r$ processed is also known as the number of bed volumes (BV) of oil processed. For a continuous column method, the volume of ion-exchange resin is fixed and a sub-theoretical volume of oil is passed through the ion-exchange resin. Metal-containing biomass-derived pyrolysis oil is contacted with about 0.1 to about 10 times the volume capacity ($VC_r$) of the acidic ion-exchange resin, preferably about 1 to about 5 VCr.

Using the various embodiments of the process 10, the total metal concentration is reduced, including the alkali metals such as sodium (Na), potassium (K) and cesium (Cs) as well as the alkaline earth metals, magnesium (Mg), calcium (Ca) and strontium (Sr). The transition metals, iron (Fe), manganese (Mn) and nickel (Ni), may also be reduced.

Resin efficiency, also referred to as ion-exchange efficiency ($IX_{eff}$), is defined as the fraction of metals removed from the liquid biomass-derived pyrolysis oil relative to the theoretical capacity of the resin and is determined as follows:

$$IX\text{eff}=(\Sigma((C_{if}-C_{ip})*V_i/\text{MW}_i*1000*M_f))/(TC_r*M_r),$$

where $C_{if}$ and $C_{ip}$ are the concentration of metal i expressed in terms of grams of metal i per gram of oil in the feed (biomass-derived pyrolysis oil) and product (low metal biomass derived pyrolysis oil), respectively, $M_f$ is the mass of feed oil in grams, $MW_i$ is the molecular weight of metal i in g/mol, $V_i$ is the valency (charge) of metal i in solution, $TC_r$ is the theoretical capacity of resin r and $M_r$ is the mass in grams of resin r utilized. If it is assumed that a single metal ion neutralizes one resin exchange site regardless of ion charge, then the valance of the individual ions ($V_i$) is assigned as 1 for all metals. The higher the exchange efficiency, the better. Theoretical resin capacity multiplied by the ion exchange efficiency provides the actual capacity, which is the amount of ion-exchange resin needed to actually deionize a given amount of biomass-derived pyrolysis oil. The lower the experimental resin capacity, i.e., the lower the concentration of acid sites (eq/L), the larger the column needs to be, i.e., the greater the resin volume needed to deionize the biomass-derived pyrolysis oil.

Ion-exchange resins useful in the process 10 according to exemplary embodiments of the present invention are strongly acidic cation-exchange resins. Preferably, the resin is used in the protonated form, i.e., all of the active groups are —$SO_3H$. Neutralized sulfonic acid resins, in which some or all of the protons have been exchanged by a cation such as lithium, sodium, potassium, magnesium, and calcium are also suitable. However, if resins are supplied with an alternate counterion (i.e sodium, $Na^+$), then the acid form may be generated prior to use by treatment with aqueous acid (such as hydrochloric, nitric, or sulfuric acid, etc.) This is commonly known in the art as ion-exchange resin activation. Preferably, the resin comprises sulfonated copolymers of styrene.

Preferred sulfonic acid resins for use in the method of the invention are macroreticular resins. As used herein, "macroreticular resins" are made of two continuous phases—a continuous pore phase and a continuous gel polymeric phase. The continuous gel polymeric phase is structurally composed of small spherical microgel particles agglomerated together to form clusters, which, in turn, form interconnecting pores. The surface area arises from the exposed surface of the microgel clusters. Macroreticular ion exchange resins can be made with different surface areas ranging from 7 to 1500 $m^2/g$, and average pore diameters ranging from about 5 to about 10000 nm.

Gel-type resins may also be used. As used herein, "gel-type resins" are generally translucent. There are no permanent pore structures for the gel-type resins. The pores are generally considered to be molecular-scale micropores. The pore structures are determined by the distance between the polymer chains and crosslinks which vary with the crosslink level of the polymer, the polarity of the solvent, and the operating conditions. Macroreticular resins are preferable for continuous column ion-exchange applications where resin swelling/shrinking should be minimized, while gel-type resins are preferred for batch ion-exchange applications, but either type may be used in either application.

Suitable acidic ion-exchange resins include those manufactured by Dow Chemical Co., Midland, Mich. (USA) under the tradenames/trademarks DOWEX® MARATHON C, DOWEX® MONOSPHERE C-350, DOWEX® HCR-S/S, DOWEX® MARATHON MSC, DOWEX® MONOSPHERE 650C, DOWEX® HCR-W2, DOWEX® MSC-1, DOWEX® HGR NG (H), DOWE® DR-G8, DOWEX® 88, DOWEX® MONOSPHERE 88, DOWEX® MONOSPHERE C-600 B, DOWEX®MONOSPHERE M-31, DOWEX® MONOSPHERE DR-2030, DOWEX® M-31, DOWEX® G-26 (H), DOWEX® 50W-X4, DOWEX® 50W-X8, DOWEX® 66, those manufactured by Rohm and Haas, Philadelphia, Pa. (USA) under the tradenames/trademarks Amberlyst® 131, Amberlyst® 15, Amberlyst® 16, Amberlyst® 31, Amberlyst® 33, Amberlyst® 35, Amberlyst® 36, Amberlyst® 39, Amberlyst® 40 Amberlyst® 70, Amberlite® FPC11, Amberlite® FPC22, Amberlite® FPC23, those manufactured by Brotech Corp., Bala Cynwyd, Pa. (USA) under the tradnames/trademarks Purofine® PFC150, Purolite® C145, Purolite® C150, Purolite® C160, Purofine® PFC100, Purolite® C100, and those manufactured by Thermax Limited Corp., Novi, Mich. (USA) under the tradename/trademark Monoplus™ S100 and Tulsion® T42.

Referring again to FIG. 1, the low metal, water-containing biomass-derived pyrolysis oil is then removed from the used ion-exchange resin (hereinafter the "spent ion-exchange resin") (step 16). In a batch ion-exchange, the low metal, water-containing biomass-derived pyrolysis oil may be removed by filtration, decantation, or other known method. In continuous column ion exchange, the low metal, water-containing biomass-derived pyrolysis oil is removed from the spent ion-exchange resin when the low metal, water-containing biomass-derived pyrolysis oil elutes from the column gravimetrically or under positive pressure.

Residual low metal, water-containing biomass-derived pyrolysis oil (hereinafter "residual oil") on the spent ion-exchange resin may be removed and recovered (step 424). The residual oil may be removed and recovered by purging the ion-exchange column with gas such as nitrogen, air or the like (not shown). Alternatively, at least a portion of the residual oil may be removed by washing the spent ion-exchange resin with an alcohol (step 414) (hereinafter described with respect to FIG. 4). The alcohol is referred to herein as an "alcohol ion-exchange regenerant". The step of removing residual oil (step 424) may also be the washing step (step 414) of the regeneration method 400 to regenerate the spent ion-exchange resin as hereinafter described and illustrated in FIGS. 1, 3, and 4. For ease of reference, the alcohol is referred to as an "alcohol ion-exchange regenerant" whether or not the spent ion-exchange resin is regenerated. The alcohol ion-exchange regenerant is miscible with the oil at the operating temperature. The alcohol ion-exchange regenerant may be a recovered azeotrope-forming liquid from the azeotropic distillation process, hereinafter described, or an alcohol provided from another source (step 420). Suitable exemplary alcohols include methanol, ethanol, and combinations thereof. In addition, while alcohols have been described for use as alcohol ion-exchange regenerants, the invention is not so limited. Other liquids that are miscible with the oil at the operating temperature, while not technically alcohols, such as acetone and 2-butanone can be used singly, or in combination, as alcohol ion-exchange regenerants in addition to or instead of alcohols. Typically about 0.1 to about 10 column volumes of the alcohol ion-exchange regenerant is used to recover the residual oil. Small amounts of residual oil may still remain on the ion-exchange resin and are therefore considered a loss. The alcohol ion-exchange regenerant preferably elutes from the ion-exchange column to blend with the low metal, water-containing biomass-derived pyrolysis oil as a phase stabilizer, thus increasing the storage stability of the low metal, water-containing biomass-derived pyrolysis oil and the subsequently produced low metal, low water biomass-derived pyrolysis oil. While use of the alcohol ion-exchange regenerant to remove the residual oil after continuous column ion exchange has been described, the invention is not so limited. The alcohol ion-exchange regenerant may also be used to remove residual oil from the spent ion-exchange resin following batch ion-exchange and act as a phase stabilizer in the batch-recovered low metal, water-containing biomass-derived pyrolysis oil.

Referring again to FIG. 1, method 200 continues with the process 100 for the production of low metal, low water biomass-derived pyrolysis oil. Process 100 begins by providing the low metal, water-containing biomass-derived pyrolysis oil from step 16 (and optionally step 424) (step 102) and distilling the low metal, water-containing biomass-derived pyrolysis oil in a distillation apparatus by azeotropic distillation (step 104). The low metal, water-containing biomass-derived pyrolysis oil and one or more azeotrope-forming liquids are introduced into a distillation apparatus (not shown) maintained at an effective temperature to form an azeotrope. The one or more azeotrope-forming liquids are added to the low metal, water-containing biomass-derived pyrolysis oil such that an azeotrope with water forms upon azeotropic distillation. As used herein, an "azeotrope" is a mixture of two or more substances whose liquid and gaseous forms have the same composition (at a certain pressure). The azeotrope is removed leaving low metal, low water biomass-derived pyrolysis oil. The wt % water in the starting, intermediate, and product biomass-derived pyrolysis oils may be measured, for example, by Karl Fischer Reagent Titration Method (ASTM D1364) as known to one skilled in the art.

The minimum effective temperature is at or above the boiling temperature of the azeotrope to be formed, as shown below in Table 1. The low metal, water-containing biomass-derived pyrolysis oil may be introduced into the distillation apparatus as a single stream as shown or as more than one stream. The added azeotrope-forming liquid(s) utilized to form the azeotrope with water (from the low metal, water-containing biomass-derived pyrolysis oil) during distillation may be added to the distillation apparatus as a separate stream or multiple streams, in which case the azeotrope-forming liquid(s) can be added below the lowest feed point of the starting low metal, water-containing biomass-derived pyrolysis oil, or it may be mixed with the low metal, water-containing biomass-derived pyrolysis oil stream(s) before it is fed to the distillation apparatus. Alternatively, both methods of introduction may be used. If the azeotrope-forming liquid is added below the lowest feed point of the starting low metal, water-containing biomass-derived pyrolysis oil, less azeotrope-forming liquid may be needed and the removal of water from the low metal, water-containing biomass-derived pyrolysis oil through azeotropic distillation may be increased. If two azeotrope-forming liquids are added to the low metal, water-containing biomass-derived pyrolysis oil, a ternary azeotrope with the water is formed. To form binary azeotropes with water, one azeotrope-forming liquid may be added to the low metal, water-containing biomass-derived pyrolysis oil.

Effective azeotrope-forming liquids for preparing low water biomass-derived pyrolysis oil include toluene, ethanol, acetone, 2-propanol, cyclohexane, 2-butanone, octane, benzene, ethyl acetate, and combinations thereof. Exemplary suitable azeotropes include binary azeotropes such as ethanol/water, toluene/water, acetone/water, 2-propanol/water, cyclohexane/water, 2-butanone/water, and octane/water and ternary azeotropes such as ethanol/toluene/water, 1-butanol/octane/water, benzene/2-propanol/water, ethanol/2-butanone/water, and ethanol/ethyl acetate/water. The weight ratio and boiling point of each of these azeotropes at atmospheric pressure is shown below in Table 1:

TABLE 1

| Azeotrope | Weight Ratio (1 atm) | Boiling Point, ° C. (1 atm) |
|---|---|---|
| Ethanol/Water | 96:4 | 78 |
| Toluene/Water | 80:20 | 85 |
| Acetone/Water | 88:12 | 56 |
| 2-propanol/Water | 88:12 | 80 |
| Cyclohexane/Water | 92:8 | 70 |
| 2-butanone/Water | 89:11 | 73 |
| Octane/Water | 72:26 | 90 |
| Ethanol/Toluene/Water | 37:51:12 | 74 |
| 1-butanol/octane/Water | 15:25:60 | 86 |
| Benzene/2-propanol/Water | 72:20:8 | 66 |
| Ethanol/2-butanone/Water | 14:75:11 | 73 |
| Ethanol/ethyl acetate/Water | 8:83:9 | 70 |

Source: Gorden, Arnold J.; Ford, Richard A., The Chemist's Companion: A Handbook of Practical Data Techniques and References, 1972, John Wiley and Sons (New York); pp. 24-30.

Azeotrope selection is driven by the amount and cost of the azeotrope-forming liquids, the desired boiling temperature, and the compatibility of the azeotrope-forming liquid with the low water biomass-derived pyrolysis oil. "Compatibility" as used herein means that the azeotrope-forming liquid is co-soluble with the low metal biomass-derived pyrolysis oil, i.e., that there is no phase separation upon mixing of the low-metal biomass-derived pyrolysis oil and the azeotrope-forming liquid(s). While certain azeotrope-forming liquids and azeotropes have been identified, the present invention is not so limited. Other azeotrope-forming liquids and azeotropes may be used if they form an azeotrope with water alone or with water in combination with other azeotrope-forming liquids.

The amount of azeotrope-forming liquid(s) and the minimum temperatures required for water removal depend on the desired level of water reduction and the specific azeotrope to be used. For example, the minimum amount of the azeotrope-forming liquid(s) added to the low metal, water-containing biomass-derived pyrolysis oil subjected to the azeotropic distillation may be determined based on the wt % of water in the low metal, water-containing biomass-derived pyrolysis oil and the desired wt % water in the low metal, low water biomass-derived pyrolysis oil. The difference between these two numbers is the wt % of water that must be removed. The wt % of water that must be removed multiplied by the weight of the low metal, water-containing biomass-derived pyrolysis oil provides the weight of the water that must be removed from the low metal, water-containing biomass-derived pyrolysis oil to reach the desired wt % water in the low metal, low water biomass-derived pyrolysis oil. The weight ratio of the water and azeotrope-forming liquid in the azeotrope can be used to calculate the minimum amount of each of the azeotrope-forming liquids to be added (in kilograms) to the low metal, water-containing biomass-derived pyrolysis oil according to the following calculations:

> weight ratio of azeotrope-forming liquid to water in azeotrope×mass (in kg) of water to be removed from low metal, water-containing biomass-derived pyrolysis oil=Minimum amount of azeotrope-forming liquid to be added (in kg) to the low metal, water-containing biomass-derived pyrolysis oil > The mass (in kg) of water to be removed=$M_f*([H_2O]_i-[H_2O]_f)/(1-[H_2O]_f)$, wherein:
$M_f$=mass of low metal, water-containing biomass-derived pyrolysis oil (in kilograms); and
$[H_2O]_i$ and $[H_2O]_f$=water concentration in grams of water per gram of oil of the initial (low metal, water-containing biomass-derived pyrolysis oil) and final pyrolysis oil (low metal, low water) respectively.

For example, where 1 kg of low metal, water-containing biomass-derived pyrolysis oil ("starting oil") contains 25 wt % water as determined, for example, by Karl Fischer titrations, i.e., 0.250 kg, and the desired water content of the low metal, low water biomass-derived pyrolysis oil ("target oil") contains 15 wt % water, the water to be removed=1 kg*(0.25−0.15)/(1−0.15)=0.118 kg water. To form an ethanol/toluene/water azeotrope having a weight ratio of 37:51:12 as identified in Table 1 above, the amount of ethanol and toluene to be added to 1 kg of low metal, water-containing biomass-derived pyrolysis oil is calculated as follows:

> Ethanol to be added=37/12×0.118 kg=about 0.364 kg

> Toluene to be added=51/12×0.118 kg=about 0.501 kg.

While the above calculations provide the minimum amount of the one or more azeotrope-forming liquids to be added to the low metal, water-containing biomass-derived pyrolysis oil, in practice, an excess amount of the one or more of the azeotrope-forming liquids is added to drive the water reduction and maintain phase homogeneity. The one or more azeotrope-forming liquid(s) to be added in excess is selected based on compatibility with the target oil as well as the relative costs of the azeotrope-forming liquids. The amount to be added in excess is determined experimentally.

The temperature in the distillation apparatus is maintained at least at the boiling temperature of the selected azeotrope. The temperature may be increased above the minimum boiling temperature to increase the distillation rate. However, the temperature in the distillation apparatus preferably is kept at least at the boiling temperature of the selected azeotrope but as low as possible to remove water (normal boiling point=100° C.) while also avoiding solids formation. Heat is supplied to the distillation apparatus by any conventional means. The temperatures may be different in the top and bottom of the distillation apparatus and where the feed stream enters the distillation apparatus. Depending on the distillation apparatus, there may also be a temperature gradient in which the temperature is lower at the top of the distillation apparatus and higher at the bottom. However, such temperature differences are not required.

The pressure of the azeotrope is typically defined at 1 atmosphere. Alternate pressures (0.1 atm (subatmospheric) to about 10 atmospheres (superatmospheric)) may be used but the azeotrope composition may need to be adjusted by adding more or less of an azeotrope-forming liquid. Absolute pressures of the vapor above the boiling liquid near 1 atmosphere, about 0.8 to about 1.2 atmosphere, are preferred. The pressure is maintained by application of vacuum (for less than one atmosphere) or the use of a back pressure regulating device (for greater than one atmosphere).

The azeotropic distillation process performed on the low metal, water-containing biomass-derived pyrolysis oil produces low metal, low water biomass-derived pyrolysis oil and the azeotrope. Process 100 continues with the step of removing the azeotrope, such as in the form of overhead vapors, from the distillation apparatus after its formation (step 106). The low metal, low water biomass-derived pyrolysis oil may be removed from a bottom portion of the distillation apparatus (step 108). The distilling step may be repeated with the low metal, low water biomass-derived pyrolysis oil to further reduce the water content, as illustrated by dotted lines in process 100. The low metal, low water biomass-derived pyrolysis oil may then be sent for further processing into biofuel.

While ion-exchange prior to distillation has been described, the invention is not so limited. Ion-exchange following distillation may also be performed to produce low metal, low water biomass-derived pyrolysis oil. In this case, low water biomass-derived pyrolysis oil produced from process 100 then undergoes ion-exchange in process 10 to produce low metal, low water biomass-derived pyrolysis oil.

Figure 2:
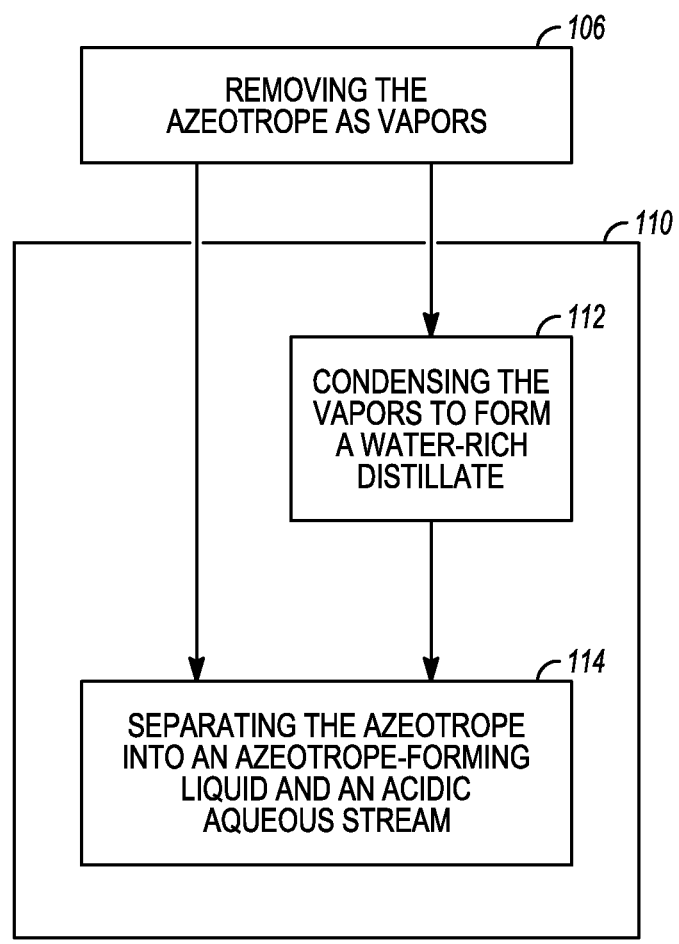
FIG. 2 is a flow diagram of a process for recovering a distillation product for use in the method of FIG. 1 and regenerating the ion-exchange resin.

Next, referring to FIGS. 1 and 2, in an exemplary embodiment, distillation product(s) comprising recovered azeotrope-forming liquids and an acidic aqueous stream are then recovered (process 110). In this regard, the azeotrope, such as in the form of vapors, may flow to a condenser (not shown) where they are condensed into a liquid water rich distillate, the amount of water present being due to the formation of the azeotrope having a minimum atmospheric boiling point at which the distillation apparatus was maintained (step 112). The distillation products may be recovered from the water rich distillate or directly from the overhead vapors of the azeotrope.

The distillation products are recovered by separating the azeotrope (step 114) into the azeotrope-forming liquid(s) and the acidic aqueous stream. The acidic aqueous stream comprises the water that was removed from the low metal, water-containing biomass-derived pyrolysis oil and was mixed with acids typically found in such oil. The azeotrope separation step may be performed by methods well known in the art. Depending on the azeotrope used, such methods may include distilling the azeotrope at elevated or reduced pressure to change the azeotrope composition, decanting (i.e., toluene/water and octane/water separate into two liquid phases at low temperature), liquid-liquid extracting, treating with desiccants including zeolites and non-zeolitic molecular sieves, and contacting the azeotrope with a polymeric or inorganic membrane to separate the acidic aqueous stream from the azeotrope-forming liquids. The membrane is selected to allow passage of either the water component (hydrophilic) (the acidic aqueous stream) or the organic azeotrope-forming liquid(s) (hydrophobic) in the azeotrope. For example, a membrane separation of an ethanol/water azeotrope can be achieved using zeolite membranes (hydrophilic and hydrophobic), as well as polypropylene, sulfonated polystyrene, and polyethylenimine membranes or the like. For a ternary azeotrope, additional steps may be used to separate two azeotrope-forming liquids. The azeotrope-forming liquids may be recycled to be used again in the azeotropic distillation process, as illustrated in FIG. 1, and if alcohols, may be reused as alcohol ion-exchange regenerants as previously and hereinafter described. The acidic aqueous stream may be used as an acidic ion-exchange regenerant, as hereinafter described. As also illustrated in FIG. 1, the distillation products recovered in step 110 may also be part of a waste stream (step 520) or recycled for other uses (step 522).

Figure 3:
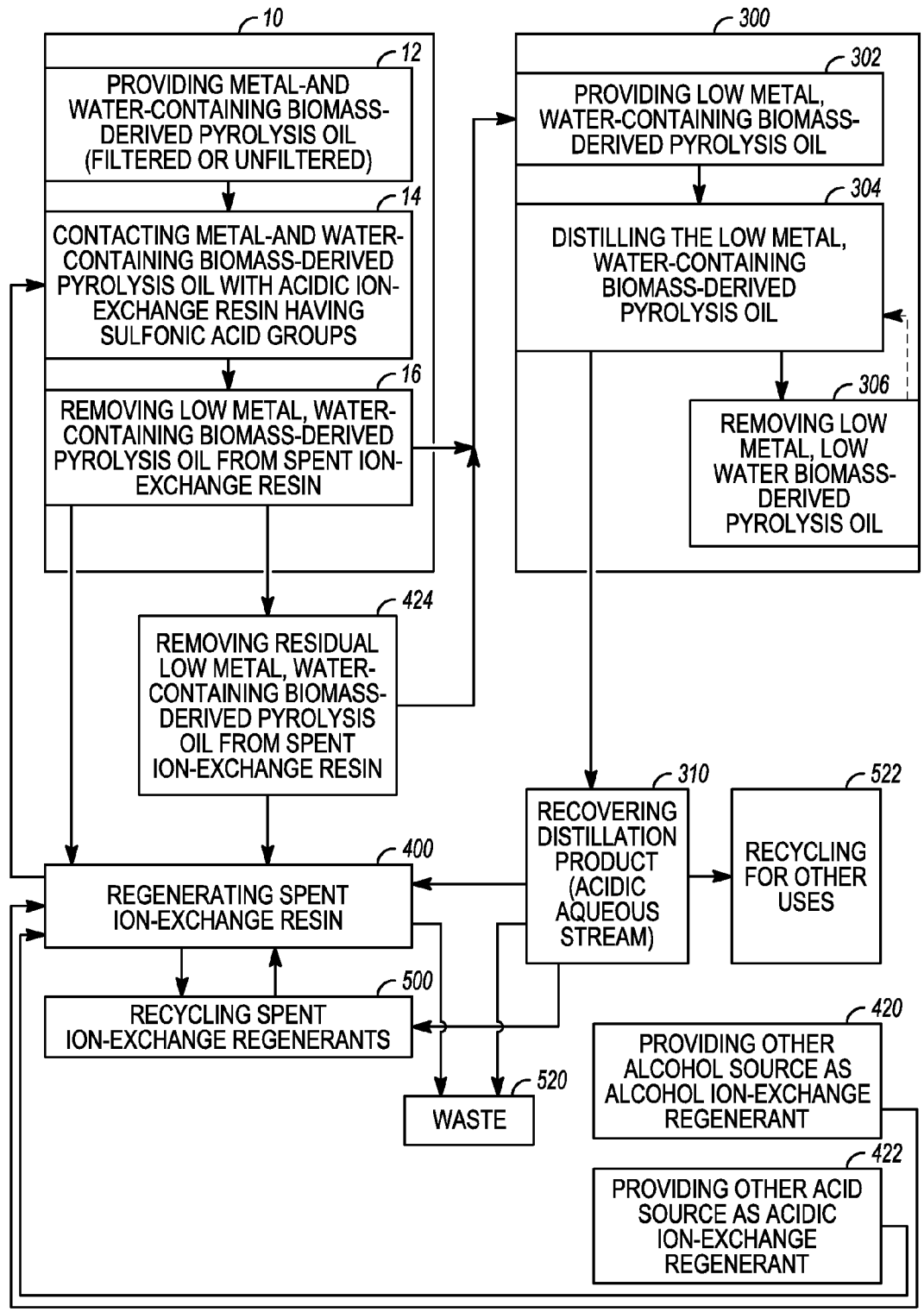
FIG. 3 is a flow diagram of a method for producing low metal, low water biomass-derived pyrolysis oil and regenerating and reusing an ion-exchange resin in such method, according to another exemplary embodiment of the present invention.

In accordance with yet another exemplary embodiment of the present invention, as shown in FIG. 3, a method 300 of producing low metal, low water biomass-derived pyrolysis oil comprises integrating process 10 for producing low metal biomass-derived pyrolysis oil with a distillation process other than azeotropic distillation that removes water from the low metal, water-containing biomass-derived pyrolysis oil. After low metal, water-containing biomass-derived pyrolysis oil is produced from process 10, as described above, the low metal, water-containing biomass-derived pyrolysis oil (provided in step 302), which may contain the residual oil of step 424 (of FIG. 1) is subjected to a vacuum, gas-assisted, or atmospheric distillation process in a distillation apparatus (step 304). Low metal, low water biomass-derived pyrolysis oil is then removed from the distillation apparatus (step 306).

Preferably, the removal of water from the low metal, water-containing biomass-derived pyrolysis oil is performed by azeotropic, vacuum, and/or gas-assisted distillation processes. Azeotropic, vacuum, and gas-assisted distillation processes permit the removal of water from low metal, water-containing biomass-derived pyrolysis oil without having to heat the oil to at least 100° C. (the boiling point of water at one atmosphere) to remove the water, i.e., such processes allow atmospheric distillation at lower temperatures. The use of lower temperatures to remove the water from the oil substantially prevents solidification (phase separation) and/or charring of the oil that is experienced at elevated temperatures (typically about 150° C.). Therefore, such distillation processes contribute to more flexible temperature requirements for the removal of water from low metal, water-containing biomass-derived pyrolysis oil. The low metal, low water biomass-derived pyrolysis oil produced using such distillation processes may be more viscous, but may be heated to a temperature to decrease viscosity. While conventional atmospheric distillation as known in the art may be used, i.e. boiling the low metal biomass-derived pyrolysis oil at least at the normal boiling point of 100° C. at one atmosphere to remove the water therein, its use is less desired because of the tendency of the oil to solidify and/or char at higher temperatures.

Vacuum distillation is performed at lower than atmospheric pressure to lower the boiling point of the water in the low metal, water-containing biomass-derived pyrolysis oil so that water therein may be removed by heating the low metal, water-containing biomass-derived pyrolysis oil at least to the lower boiling point of water at that reduced pressure. The boiling point of water at that pressure may be determined by consulting temperature/pressure charts that are available from, for example, the National Bureau of Standards (NBS)/National Research Council (NRC).

Vacuum may be applied by a vacuum pump, aspirator, or the like. In a preferred embodiment, the low-metal, water-containing biomass-derived pyrolysis oil is heated to about 65° C. at a vacuum of about 0.05 to about 0.95 atm (absolute pressure) until the desired amount of water is removed. Typically, about 5 to about 85% of the water in the low metal, water-containing biomass-derived pyrolysis oil is removed. This results in a low metal, low water biomass-derived pyrolysis oil that is about 5 to about 28 wt % water depending on the starting water content of the metal-containing, water-containing biomass-derived pyrolysis oil.

Gas-assisted distillation uses a standard distillation column with an inert gas such as nitrogen, air, argon, helium, hydrogen or other gas passing into and over the low metal, water-containing biomass-derived pyrolysis oil while heating the low metal biomass-derived pyrolysis oil to a selected temperature of about 30° C. to about 90° C., preferably about 70° C. at a flow rate of about 0.1 to about 100 liters (L) gas/L oil/minute, preferably about 0.5 to about 4 L gas/L oil/min. Gas-assisted distillation functionally reduces the vapor pressure of the oil, thus resulting in more water in vapor phase so that it can be removed from the low metal biomass-derived pyrolysis oil at less than 100° C. The rate at which the water is removed is limited by the vapor pressure of water at the selected temperature, the gas flow rate, and the liquid volume to be distilled. The gas flow rate (controlled by a mass flow controller or valve) and selected temperature may be varied depending on the desired rate of water removal.

Regardless of the distillation method used, a distillation product comprising the water removed from the low metal, water-containing biomass-derived pyrolysis oil may be recovered from the distillation process (step 310). The water contains acids from the low metal, water-containing biomass-derived pyrolysis oil to form an acidic aqueous stream. The acidic aqueous stream may be used as an acidic ion-exchange regenerant to help regenerate the spent ion-exchange resin in method 400, as hereinafter described. The acidic aqueous stream may also be disposed in a waste stream 520 and/or recycled for other uses (step 522).

Figure 4:
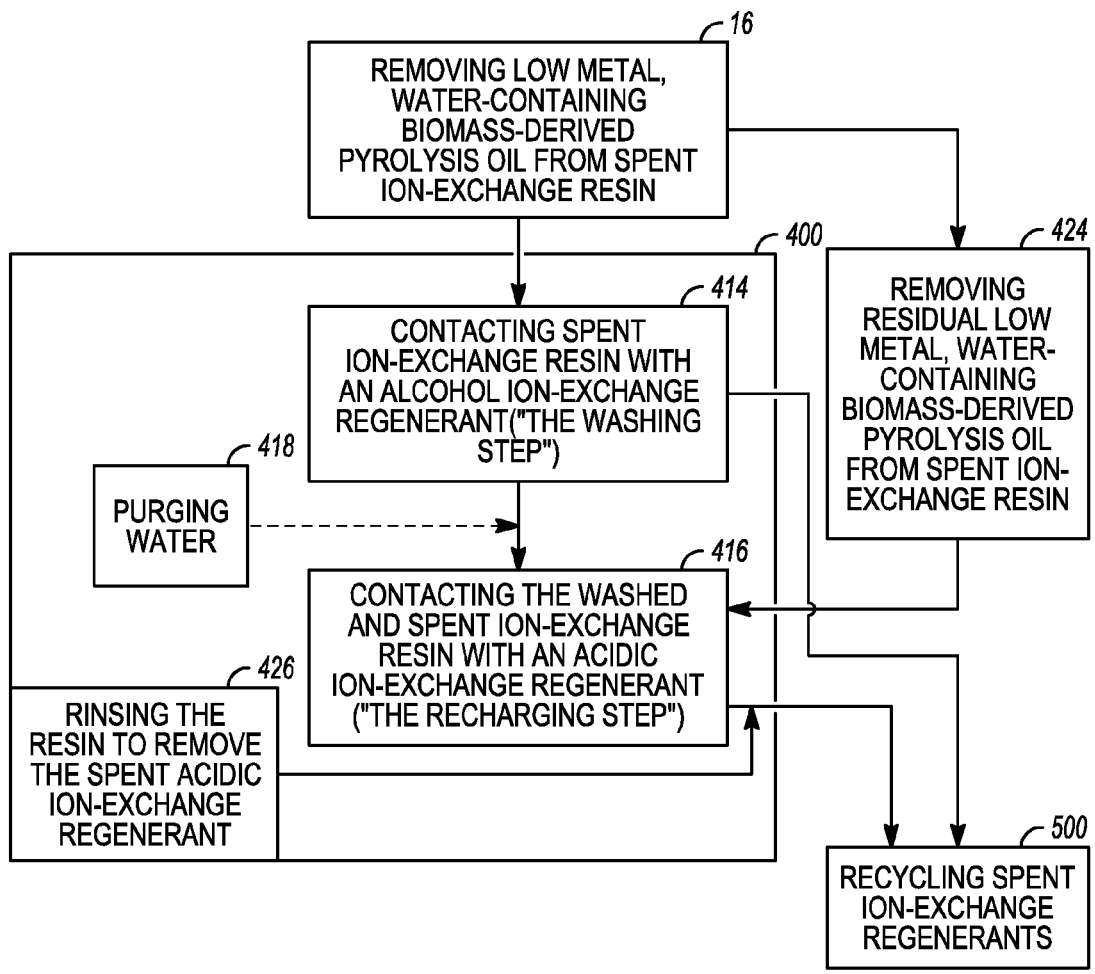
FIG. 4 is a flow diagram of a method for regenerating a spent acidic ion-exchange resin using an alcohol ion-exchange regenerant and an acidic ion-exchange regenerant, according to yet another exemplary embodiment of the present invention.

As shown in FIGS. 1 and 3, the spent acidic ion-exchange resin from process 10 containing bound metal ions may be regenerated in method 400. FIG. 4 is a simplified flow diagram that illustrates the method 400 for regeneration of the acidic ion-exchange resin following ion-exchange of metal- and water-containing biomass-derived pyrolysis oil in process 10. The regenerated ion-exchange resin may then be recycled. "Recycling" of a regenerated ion-exchange resin as used herein means to reuse in a subsequent ion-exchange process as part or all of the ion-exchange resin. As used herein, "regenerating" or "regeneration" of a spent ion-exchange resin means returning the spent ion-exchange resin to its acidic protonated form in which the active groups are —SO$_3$H. It is to be appreciated that regeneration of the spent ion-exchange resin may be performed whether or not distillation follows ion-exchange.

As shown in FIG. 4, after removing the low metal, water-containing biomass-derived pyrolysis oil from the spent ion-exchange resin (step 16), the spent ion-exchange resin is regenerated (method 400) by contacting the spent ion-exchange resin with an alcohol ion-exchange regenerant to wash the spent ion-exchange resin and thereafter contacting the washed, spent ion-exchange resin (step 416) with an acidic ion-exchange regenerant to recharge the resin by displacing the metal ions thereon with hydrogen ions. The acidic ion-exchange regenerant is removed from the resin by rinsing the resin with water and/or alcohol prior to introducing fresh oil for ion-exchange (step 426). If alcohol is used to rinse away the acidic ion-exchange regenerant, it may be alcohol recycled from a process and method described herein in accordance with exemplary embodiments. As described previously, the step of removing residual oil (step 424) may serve as the washing step (step 414) of the regeneration method 400 to regenerate the spent ion-exchange resin. Contacting the spent ion-exchange resin with the alcohol ion-exchange regenerant between ion-exchange of the metal- and water-containing biomass-derived pyrolysis oil and the acidic ion-exchange regenerant makes the spent ion-exchange resin regenerable and provides a transition in the ion-exchange column between the metal- and water-containing biomass-derived pyrolysis oil and the acidic ion-exchange regenerant. It is beneficial not to contaminate the oil with acidic ion-exchange regenerant due to the impact of the acid on downstream operations, or to contaminate the acidic ion-exchange regenerant with the oil because this will impact the ability to recycle or dispose of the acidic ion-exchange regenerant. In addition, the alcohol ion-exchange regenerant substantially prevents column plugging by the residual oil and the acidic ion-exchange regenerant, and improves the phase stability of the low metal, water-containing biomass-derived pyrolysis oil produced by process 10 and the low metal, low water biomass-derived pyrolysis oil produced by processes 200 and 300, as previously described.

When the alcohol and acidic ion-exchange regenerants are no longer useful for regeneration, they are "exhausted". A waste stream 520 containing the exhausted alcohol/acidic ion-exchange regenerants may be formed. While waste stream 520 is illustrated in FIGS. 1 and 3 as a single stream receiving waste from both steps 110/310 and 400, waste stream 520 may be more than one stream. Alternatively, the method 400 of regenerating the spent ion-exchange resin may further comprise purging water through the washed and spent ion-exchange resin between the washing step 414 and recharging step 416 (step 418). The water purge separates the alcohol ion-exchange regenerant waste effluent stream from the acidic ion-exchange regenerant waste effluent stream forming separate alcohol and acidic ion-exchange regenerant waste effluent streams. The separate streams enable easier disposal of the waste effluent than does the single alcohol/acidic ion-exchange regenerant effluent waste stream formed without the water purge.

While the use of alcohol and acidic distillation products as the alcohol and acidic ion-exchange regenerants, respectively, has been described, the invention is not so limited. The alcohol and acidic ion-exchange regenerants may be provided from other alcohol sources and acid sources (steps 420 and 422), respectively, and used in addition to, or instead of the ion-exchange regenerants from the distillation processes described herein. That is, the recovered alcohol and acidic distillation products may be used as only a portion, respectively, of the alcohol and acidic ion-exchange regenerant streams. With respect to method 300, while the distillation product of method 300 can comprise the acidic ion-exchange regenerant, the "other" alcohol source (step 420) provides the alcohol ion-exchange regenerant. As the acids in the acidic aqueous stream are weak acids compared to conventional strongly acidic ion-exchange regenerants, such as sulfuric acid and hydrochloric acid, the strength of the acidic aqueous stream may be adjusted, for example, by adding acids such as sulfuric acid, hydrochloric acid or the like from the other acid source (step 422) to make the acidic aqueous stream useful for regenerating the spent ion-exchange resin. The additional acid may be added to the acidic aqueous stream or it may be used sequentially. Larger volumes of the acidic aqueous stream may also be needed to regenerate the spent ion-exchange resin. As the acidic aqueous stream is made on-site, a large volume is readily available. Two different concentrations (i.e., a low and a high concentration) of the acidic ion-exchange regenerant may be used to help avoid precipitation of low solubility salts in the oil.

While an alcohol recovered from azeotropic distillation of a low metal, water-containing biomass-derived pyrolysis, an alcohol from another source, or a combination thereof has been described for use as the alcohol ion-exchange regenerant, the invention is not so limited. The alcohol recovered from azeotropic distillation of a metal- and water-containing biomass-derived pyrolysis oil (process 100 in FIG. 1) may also be used as the alcohol ion-exchange regenerant. Similarly, while a recovered acidic aqueous stream from distillation of a low-metal, water-containing biomass-derived pyrolysis oil, an acid from an acid source, or a combination thereof has been described for use as the acidic ion-exchange regenerant, the invention is not so limited. The acidic aqueous stream recovered from azeotropic distillation of a metal- and water-containing biomass-derived pyrolysis oil (process 100 in FIG. 1) may also be used as the acidic ion-exchange regenerant.

In one exemplary embodiment, the spent alcohol and acidic ion-exchange regenerants may be recycled (step 500). The spent alcohol ion-exchange regenerant may be recycled as the azeotrope-forming liquid in the azeotropic distillation process (step 104) (FIG. 1), as the alcohol ion-exchange regenerant to remove residual oil from the spent ion-exchange resin (step 424) (FIGS. 1 and 3-4), to regenerate a spent ion-exchange resin (method 400), as the other alcohol source (step 420), or a combination thereof. Thus, the same alcohol can be used in multiple production processes and methods. This reduces the overall cost of the process and method and reduces the overall disposal cost associated with the alcohol. The alcohol can be cycled through the azeotropic distillation process and ion-exchange processes multiple times before it is exhausted. The spent alcohol ion-exchange regenerant may contain residual water that needs to be at least partially reduced before recycling. The residual water in the spent alcohol ion-exchange regenerant may be reduced by desiccants, membranes, or the like. The spent alcohol ion-exchange regenerant may also be disposed of in the waste stream 520.

The spent acidic ion-exchange regenerant may be recycled to regenerate the spent ion-exchange resin in another cycle. The spent acidic ion-exchange regenerant, if an organic acid such as acetic acid, may also be recycled to the pyrolysis reactor (not shown) in which the biomass-derived pyrolysis oil may be produced, for example, from pyrolysis of biomass. The spent acidic ion-exchange regenerant may also be disposed of in the waste stream 520.

It is to be appreciated that low metal, low water biomass-derived pyrolysis oil having greater storage stability and higher energy density than the starting biomass-derived pyrolysis oil has been provided. Higher energy density means that the low metal, low water biomass-derived pyrolysis oil has an increased heat of combustion. The phase separation and solidification and/or charring that occurs with simple distillation at temperatures above 150° C. is substantially prevented while reducing the water content of the oil. The reduced metal and water content, along with the greater storage stability and higher energy density, increases the suitability of the low metal, low water biomass-derived pyrolysis oil as a biofuel. In addition, the regeneration and recycling of the acidic ion-exchange resin and ion-exchange regenerants simplify processing, and reduce material and disposal costs.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for the regeneration of a spent acidic ion-exchange resin and recycling thereof comprising:
    contacting the spent ion-exchange resin with an alcohol ion-exchange regenerant consisting of an alcohol;

thereafter contacting the spent ion-exchange resin with an acidic ion-exchange regenerant to recharge the acidic ion-exchange resin to produce a regenerated acidic ion-exchange resin; and contacting a metal- and water-containing biomass-derived pyrolysis oil with the regenerated acidic ion-exchange resin to produce a low metal, water-containing biomass-derived pyrolysis oil.

2. The method of claim 1, wherein the step of contacting the spent ion-exchange resin with the alcohol ion-exchange regenerant comprises leaving residual alcohol ion-exchange regenerant in the spent ion-exchange resin and the low metal, water-containing biomass-derived pyrolysis oil further comprises residual alcohol ion-exchange regenerant.

3. The method of claim 1, wherein the step of contacting the spent ion-exchange resin with the alcohol ion-exchange regenerant comprises contacting the spent ion-exchange resin with an alcohol recovered from azeotropic distillation of a metal- and water-containing biomass-derived pyrolysis oil, with an alcohol recovered from azeotropic distillation of a low metal, water-containing biomass-derived pyrolysis oil, with an alcohol from an alcohol source, or a combination thereof.

4. The method of claim 1, wherein the step of contacting the spent ion-exchange resin with the acidic ion-exchange regenerant comprises contacting the spent ion-exchange resin with a recovered acidic aqueous stream from distillation of a metal- and water-containing biomass-derived pyrolysis oil, with a recovered acidic aqueous stream from distillation of a low-metal, water-containing biomass-derived pyrolysis oil, with an acid from an acid source, or a combination thereof.

5. The method of claim 1, wherein the step of contacting the spent ion-exchange resin with the alcohol ion-exchange regenerant comprises selecting the alcohol ion-exchange regenerant from a group consisting of methanol, ethanol, acetone, 2-butanone, or a combination thereof.

6. The method of claim 1, further comprising the step of purging water through the spent ion-exchange resin between contacting the spent ion-exchange resin with an alcohol ion-exchange regenerant and contacting the spent ion-exchange resin with an acidic ion-exchange regenerant.

7. The method of claim 1, wherein the step of contacting the spent ion-exchange resin with an acidic ion-exchange regenerant to recharge the acidic ion-exchange resin to produce a regenerated acidic ion-exchange resin comprises returning the spent ion-exchange resin to an acidic protonated form in which the active groups are $SO_3H$.

8. The method of claim 1, further comprising the step of rinsing the acidic ion-exchange regenerant from the recharged acidic ion-exchange resin prior to the step of contacting the metal- and water-containing biomass-derived pyrolysis oil with the regenerated acidic ion-exchange resin.

9. The method of claim 1, further comprising the step of recycling at least one of the ion-exchange regenerants.

10. The method of claim 9, wherein the step of recycling at least one of the ion-exchange regenerants comprises using the alcohol ion-exchange regenerant as an azeotrope-forming liquid in an azeotropic distillation process, as an alcohol ion-exchange regenerant to remove residual oil from the spent ion-exchange resin, to regenerate a spent ion-exchange resin, or a combination thereof.

11. The method of claim 9, wherein the step of recycling at least one of the ion-exchange regenerants comprises reusing the acidic ion-exchange regenerant to regenerate the spent ion-exchange resin in another cycle, to be used in a pyrolysis reactor, or a combination thereof.

12. A method for the regeneration of a spent acidic ion-exchange resin and recycling thereof comprising:

contacting the spent ion-exchange resin with an alcohol ion-exchange regenerant wherein at least one component of the alcohol ion-exchange regenerant is recovered from azeotropic distillation of a metal- and water-containing biomass-derived pyrolysis oil, azeotropic distillation of a low metal, water-containing biomass-derived pyrolysis oil, or a combination thereof;

thereafter contacting the spent ion-exchange resin with an acidic ion-exchange regenerant to recharge the acidic ion-exchange resin to produce a regenerated acidic ion-exchange resin; and contacting a metal- and water-containing biomass-derived pyrolysis oil with the regenerated acidic ion-exchange resin to produce a low metal, water-containing biomass-derived pyrolysis oil.

13. The method of claim 12, further comprising the step of rinsing the acidic ion-exchange regenerant from the recharged acidic ion-exchange resin prior to the step of contacting the metal- and water-containing biomass-derived pyrolysis oil with the regenerated acidic ion-exchange resin.

14. The method of claim 12, further comprising recycling at least one of the ion-exchange regenerants as an azeotrope-forming liquid in an azeotropic distillation process, as an alcohol ion-exchange regenerant to remove residual oil from the spent ion-exchange resin, to regenerate a spent ion-exchange resin, or a combination thereof.

15. The method of claim 12, further comprising recycling at least one of the ion-exchange regenerants to regenerate the spent ion-exchange resin in another cycle, to a pyrolysis reactor, or a combination thereof.

16. A method for the regeneration of a spent acidic ion-exchange resin and recycling thereof comprising:

contacting the spent ion-exchange resin with an alcohol ion-exchange regenerant;

thereafter contacting the spent ion-exchange resin with an acidic ion-exchange regenerant to recharge the acidic ion-exchange resin to produce a regenerated acidic ion-exchange resin wherein at least one component of the acidic ion-exchange resin is a recovered acidic aqueous stream from distillation of a metal- and water-containing biomass-derived pyrolysis oil, a recovered acidic aqueous stream from distillation of a low-metal, water-containing biomass-derived pyrolysis oil, or a combination thereof; and contacting a metal- and water-containing biomass-derived pyrolysis oil with the regenerated acidic ion-exchange resin to produce a low metal, water-containing biomass-derived pyrolysis oil.

17. The method of claim 16, further comprising the step of rinsing the acidic ion-exchange regenerant from the recharged acidic ion-exchange resin prior to the step of contacting the metal- and water-containing biomass-derived pyrolysis oil with the regenerated acidic ion-exchange resin.

18. The method of claim 16, further comprising recycling at least one of the ion-exchange regenerants as an azeotrope-forming liquid in an azeotropic distillation process, as an alcohol ion-exchange regenerant to remove residual oil from the spent ion-exchange resin, to regenerate a spent ion-exchange resin, or a combination thereof.

19. The method of claim 16, further comprising recycling at least one of the ion-exchange regenerants to regenerate the spent ion-exchange resin in another cycle, to a pyrolysis reactor, or a combination thereof.

* * * * *